United States Patent
Deegan et al.

(10) Patent No.: US 8,758,218 B2
(45) Date of Patent: Jun. 24, 2014

(54) METHOD OF TREATING INCONTINENCE AND TREATMENT DEVICE INCLUDING NON-POROUS CUFF AND EXTENDING MEMBERS

(75) Inventors: Christopher Deegan, North St. Paul, MN (US); Steven McClurg, Brooklyn Park, MN (US); Mark A. Moschel, New Hope, MN (US)

(73) Assignee: Coloplast A/S, Humlebaek (DK)

( * ) Notice: Subject to any disclaimer, the term of this patent is extended or adjusted under 35 U.S.C. 154(b) by 59 days.

(21) Appl. No.: 13/453,064

(22) Filed: Apr. 23, 2012

(65) Prior Publication Data

US 2013/0281766 A1 Oct. 24, 2013

(51) Int. Cl.
*A61F 2/02* (2006.01)

(52) U.S. Cl.
USPC .......................................................... 600/30

(58) Field of Classification Search
USPC .......................................................... 600/30
See application file for complete search history.

(56) References Cited

U.S. PATENT DOCUMENTS

| | | | |
|---|---|---|---|
| 4,552,128 A | 11/1985 | Haber | |
| 5,544,664 A | 8/1996 | Benderev et al. | |
| 5,620,012 A | 4/1997 | Benderev et al. | |
| 5,702,397 A | 12/1997 | Goble et al. | |
| 5,746,763 A | 5/1998 | Benderev et al. | |
| 5,813,408 A | 9/1998 | Benderev et al. | |
| 5,836,314 A | 11/1998 | Benderev et al. | |
| 5,836,315 A | 11/1998 | Benderev et al. | |
| 5,842,478 A | 12/1998 | Benderev et al. | |
| 5,860,425 A | 1/1999 | Benderev et al. | |
| 5,934,283 A | 8/1999 | Willem et al. | |
| 6,001,104 A | 12/1999 | Benderev et al. | |
| 6,056,688 A | 5/2000 | Benderev et al. | |
| 6,077,216 A | 6/2000 | Benderev et al. | |
| 6,110,101 A | 8/2000 | Tihon et al. | |
| 6,904,916 B2 | 6/2005 | Bakane | |
| 7,326,213 B2 | 2/2008 | Benderev et al. | |
| 7,387,634 B2 | 6/2008 | Benderev | |

(Continued)

FOREIGN PATENT DOCUMENTS

WO 02058564 8/2002
WO 2007002071 1/2007

OTHER PUBLICATIONS

Office Action mailed on Mar. 27, 2013 in U.S. Appl. No. 13/676,132.

(Continued)

*Primary Examiner* — Charles A Marmor, II
*Assistant Examiner* — Shannon McBride
(74) *Attorney, Agent, or Firm* — Coloplast Corp., Coloplast A/S; Nick Baumann (57) ABSTRACT

A method of treating urinary incontinence includes making an incision and exposing tissue of a urethra. The method additionally includes inserting a non-porous sheet into the incision and forming a cuff around the urethra with the non-porous sheet by directing a first end of the non-porous sheet through a slot formed in a second end of the non-porous sheet. The method additionally includes directing an extending member that is attached to the non-porous sheet to a location exterior of a pelvis. The method further includes configuring the cuff to tighten around the urethra when pulling on the first end of the non-porous sheet, and configuring the cuff to be loosely positioned around the urethra when pulling on the extending member.

4 Claims, 7 Drawing Sheets

(56) References Cited

U.S. PATENT DOCUMENTS

| | | |
|---|---|---|
| 7,789,821 B2 | 9/2010 | Browning |
| 8,007,429 B2 * | 8/2011 | Anderson et al. ............... 600/30 |
| 8,062,205 B2 * | 11/2011 | Timm et al. ..................... 600/30 |
| 2004/0173219 A1 | 9/2004 | Bakane |
| 2006/0252980 A1 | 11/2006 | Arnal |
| 2008/0167520 A1 | 7/2008 | Benderev |
| 2009/0149883 A1 | 6/2009 | Brunsvold |
| 2009/0259092 A1 | 10/2009 | Ogdahl et al. |
| 2010/0198003 A1 | 8/2010 | Morningstar et al. |
| 2010/0198004 A1 | 8/2010 | Moschel |
| 2010/0312052 A1 | 12/2010 | Morningstar |
| 2011/0034762 A1 | 2/2011 | Paganon |
| 2011/0077455 A1 | 3/2011 | Duncan |
| 2011/0306822 A1 | 12/2011 | Witzmann et al. |
| 2012/0035627 A1 | 2/2012 | Ostrovsky |

OTHER PUBLICATIONS

Office Action mailed on Apr. 25, 2013 in U.S. Appl. No. 13/668,226.
Office Action mailed on Nov. 2, 2012 in DK Patent Application No. PA 2012 70202 Office Action mailed on Nov. 19, 2012 in DK Patent Application No. PA 2012 70219.
Final Office Action mailed on Aug. 29, 2013 in U.S. Appl. No. 13/676,132.
Extended Search Report mailed on Aug. 7, 2013 in EP application No. 13166095.3.

* cited by examiner

METHOD OF TREATING INCONTINENCE AND TREATMENT DEVICE INCLUDING NON-POROUS CUFF AND EXTENDING MEMBERS

BACKGROUND

Devices for treating urinary incontinence include slings, supports, artificial urinary sphincters and other devices that are implanted in a user to support and/or coapt the urethra.

A sling is a device that is surgically implanted to support the urethra and inhibit urine from undesirably leaking from the urethra. Slings are typically fabricated from mesh and are implanted through one or more incisions. The sling is secured to supporting tissue(s) and the tissue eventually grows through the mesh to support the urethra. The surgeon will peri-operatively determine and achieve the appropriate level of tension in the sling relative to the urethra that will post-operatively provide the user with a continent state.

An artificial urinary sphincter is generally provided as an inflatable ring or "donut" that is surgically implanted around the urethra. Some people become incontinent after having a portion or all of the prostate gland removed, which can result in a loss of some or all of the function of the prostatic urinary sphincter. An artificial urinary sphincter implanted around the compromised prostatic urinary sphincter can provide the patient with improved control of urinary function.

Improved incontinence treatment devices would be welcomed by both the patient and the surgical staff.

SUMMARY

One aspect provides an incontinence treatment device including a non-porous support and an extending member. The non-porous support has a first end portion provided with a slot and a second end portion. The second end portion is insertable through the slot to form a cuff that is configured for placement around a urethra of a user. The extending member is attached to the support at a junction located between the first end portion and the second end portion. Tension applied to the second end portion is adapted to draw the junction toward the slot to tighten the cuff and thus provide the user with a continent state. Tension applied to the extending member is adapted to draw the juncture away from the slot and expand the cuff and thus allow the user to urinate.

One aspect provides an incontinence treatment device including a non-porous sheet and an extending member attached to the non-porous sheet. The non-porous sheet has a first side spaced apart from a second side by a sheet width, a first end portion having a width that is approximately equal to the sheet width with a slot formed in the first end portion, and a second end portion that tapers to a tapered width that is less than the sheet width. The extending member has a first end that is attached to the sheet at a junction located between the first end portion and the second end portion. The extending member includes a second end that has a width that is less than the sheet width. The tapered width of the second end portion of the sheet is insertable through the slot in the first end portion to form a cuff from the non-porous sheet that is sized for placement around a human urethra. The slot has a slot width that prevents the junction from passing through the slot.

One aspect provides a method of treating urinary incontinence that includes making an incision and exposing tissue of a urethra, and inserting a non-porous sheet into the incision and forming a cuff around the urethra with the non-porous sheet by directing a first end of the non-porous sheet through a slot formed in a second end of the non-porous sheet. The method further includes directing an extending member that is attached to the non-porous sheet to a location outside of the pelvis. The method additionally includes configuring the cuff to tighten around the urethra when pulling on the first end of the non-porous sheet, and configuring the cuff to be loosely positioned around the urethra when pulling on the extending member.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification the word "coapt" means to close or to substantially close. To coapt an opening is to bring two surfaces together in close approximation such that the gap between the two surfaces is reduced or eliminated. To coapt a urethra means to substantially yet reversibly close the urethra to impede the passage of urine and provide a person with a continent state.

In this specification permanent means for as long as an incontinence treatment device is implanted into a patient. Thus, an incontinence treatment device having a permanent external portion outside of an abdominal wall of the patient provides the external portion outside of the patient for as long as the device is implanted in the patient.

In this specification a "user" is one into whom an incontinence treatment device has been implanted.

In this specification "non-porous" means a material with no through-holes. For example, a non-porous material is characterized by the absence of multiple holes that extend through the material from one surface to the other surface. Non-porous, as employed in this specification, means a material that is configured to prevent tissue growth through the implanted material.

Embodiments provide an incontinence treatment device implantable into a user and including extending members that allow the user to selectively move from a state of continence (free from urine leakage) to a state that allows urination. Tension applied to a first extending member is adapted to draw the junction toward the slot to tighten the cuff and coapt the urethra to provide the user with a continent state. Tension applied to the second extending member is adapted to draw the juncture away from the slot and loosen the cuff to relieve coaptation of the urethra and allow the user to urinate.

Figure 1:
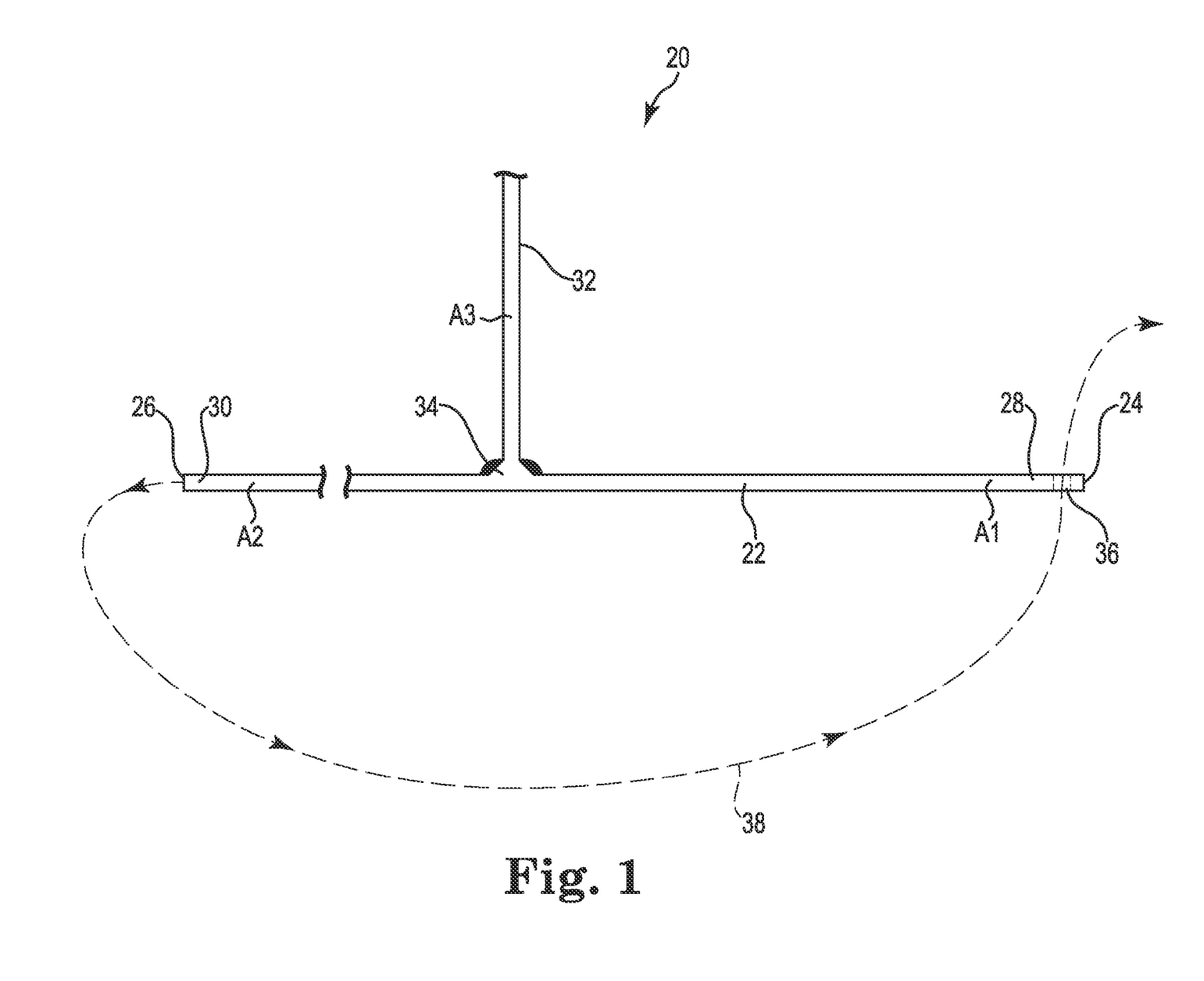
FIG. 1 is a top view of one embodiment of an incontinence treatment device.

FIG. 1 is a top view of one embodiment of an incontinence treatment device 20. The incontinence treatment device 20 (device 20) includes a support 22 in the form of a sheet or a band that extends between a first end 24 and a second end 26, with a first end portion 28 adjacent to the first end 24 and a second end portion 30 adjacent to the second end 26. An extending member 32 is attached to the support 22 at a junction 34 that is located between the first end portion 28 and the second end portion 30. The support 22 is fabricated to be non-porous such that after implantation the non-porous support 22 discourages or prevents tissue from growing onto or through the non-porous support 22.

One of the end portions 28, 30 is provided with a slot 36. For example, the first end portion 28 is provided with a slot 36 that is sized to receive the second end portion 30. Inserting the second end portion 30 through the slot 36, for example along a path 38, forms the support 22 into a cuff (40 in FIG. 2) with the second end portion 30 extending in a different direction from the extending member 32.

Prior to assembly, the device 20 provides three segments or arms: a first arm A1 that is provided by the first end portion 28 having the slot 36, a second arm A2 that is provided by the second end portion 30, and a third arm A3 that is provided by the second extending member 32.

In one embodiment, the second extending member 32 is attached at a substantially orthogonal angle to the support 22. In one embodiment, the second extending member 32 is attached to the support 22 at an angle other than 90 degrees.

Figure 2:
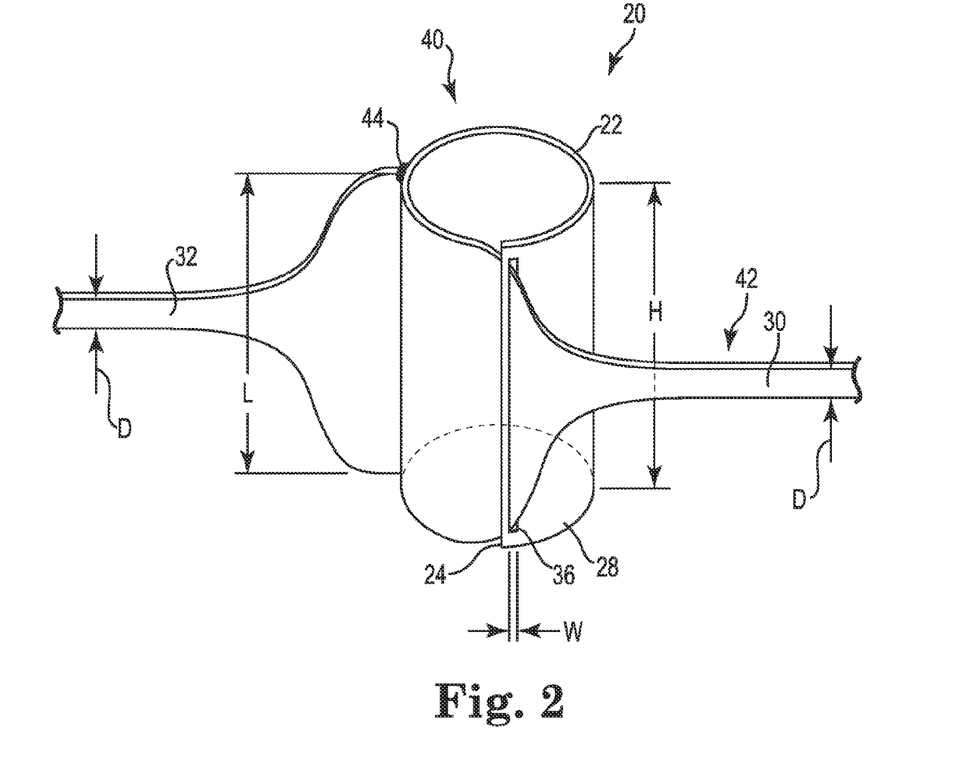
FIG. 2 is a perspective view of the incontinence treatment device illustrated in FIG. 1 as assembled to provide a cuff.
Figure 3:
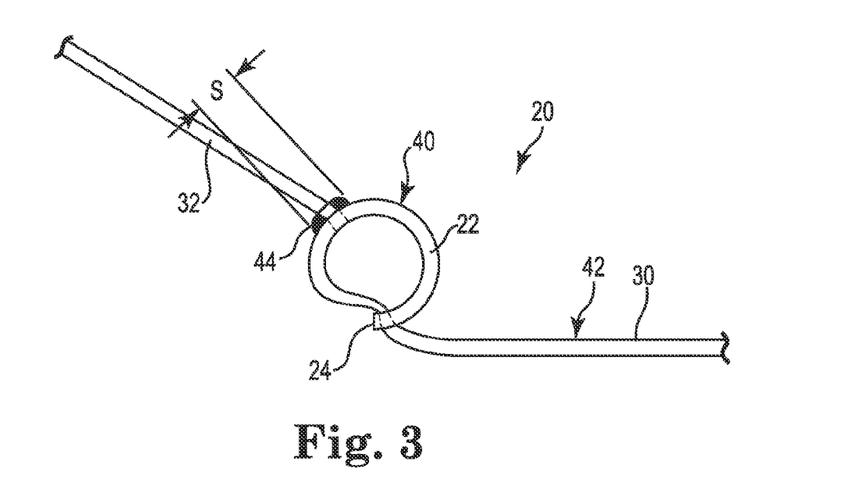
FIG. 3 is a top view of the incontinence treatment device illustrated in FIG. 2.

FIG. 2 is a perspective view and FIG. 3 is a top view of the support 22 providing a cuff 40. The cuff 40 has two adjustment arms, a tightening arm provided by the second end portion 30 and a loosening arm provided by extending member 32.

During implantation, the support 22 is placed on a first side of the urethra and the second end portion 30 is inserted through the slot 36 to form the cuff 40 around the urethra of a user. The assembled cuff 40 thus has two extending members: a first extending member 42 provided by the second end portion 30 and the second extending member 32 attached to the support 22 between the first end portion 28 and the second end portion 30.

In one embodiment, the slot 36 is formed to have a slot width W (FIG. 2). In one embodiment, the junction 34 between the member 32 and the support 22 includes a stopper 44 with a stop width S that is larger than the slot width W. The stop width S of the stopper 44 is configured to prevent the junction 34 from passing through the slot 36. In one embodiment, the slot width W is sized to prevent passage of the extending member 32 through the slot 36.

In one embodiment, the support 22 has a height H extending between opposing sides of the support 22, and each of the first extending member 42 and the second extending member 32 tapers from a first width L that is substantially equal to the height H of the support 22 to a second width D that is narrower than the height H of the support.

The support 22 is non-porous and is preferably fabricated from a synthetic material such as rubber, silicone, thermoplastic polymer, thermoset polymer, or blends of polymers or copolymers. One suitable material for fabricating the support 22 is silicone rubber. The support 22 is fabricated to be non-porous to discourage tissue growth through the surface of the support 22.

In one embodiment, at least the cuff 40 portion of the device 20 is coated with a substance that prevents tissue from attaching to or growing on a surface of the cuff 40. Tissue growth into or through the support 22 would undesirably fixate the support 22 into the patient after it is implanted. The support 22 is fabricated from materials that are non-porous and are selected to reduce or prevent the likelihood of tissue growth into or through the support 22. Although not bound to this theory, tissue is expected to grow around the cuff 40 and envelop the cuff 40 in a pocket of tissue that allows the cuff 40 to move (tighten and loosen) relative to the urethra.

In one embodiment, since the non-porous support 22 is not a mesh. In one embodiment, the non-porous support 22 has a thickness and is fabricated from, for example, a solid film having substantially uniform density through the thickness. Thus, in one embodiment, the support 22 and the resulting assembled cuff 40 are not inflatable.

Figure 4A:
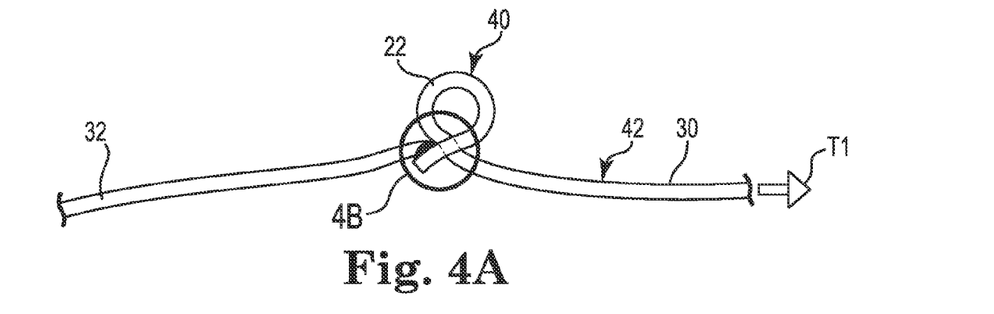
FIG. 4A is a top view and FIG. 4B is an expanded view of the incontinence treatment device illustrated in FIG. 3 with tension applied to tighten the cuff of the device.
Figure 4B:
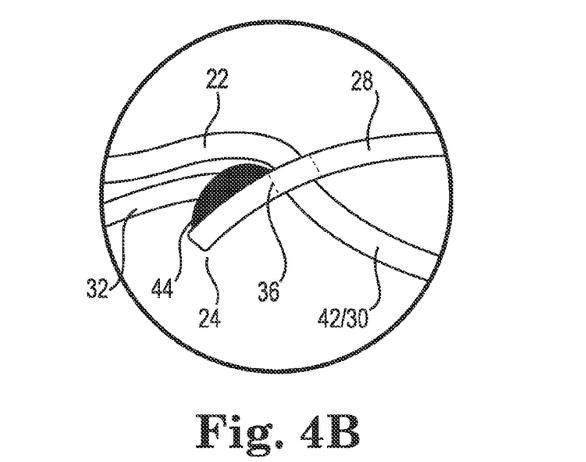

FIG. 4A is a top view and FIG. 4B is an expanded view of the cuff 40. Tension T1 illustrates a pulling force applied to the first extending member 42. The tension T1 will draw the junction 34 up to the slot 36 and reduce the diameter of the cuff 40, which is useful to coapt the urethra to provide the user with a continent state. With reference to FIG. 4B, the tension T1 applied to the first extending member 42 tightens the cuff 40 until a stopper 44 is caught by the slot 36, which prevents further collapse of the cuff 40.

The arc length of the support 22 extending from the junction 34 to the slot 36 (See FIG. 1) is selected such that the cuff 40 provides an inside diameter that is sufficient to collapse or coapt a human urethra without over compressing or eroding the urethra. The stopper 44 thus provides a feature that prevents the cuff 40 from being collapsed too tightly against the urethra.

Figure 4C:
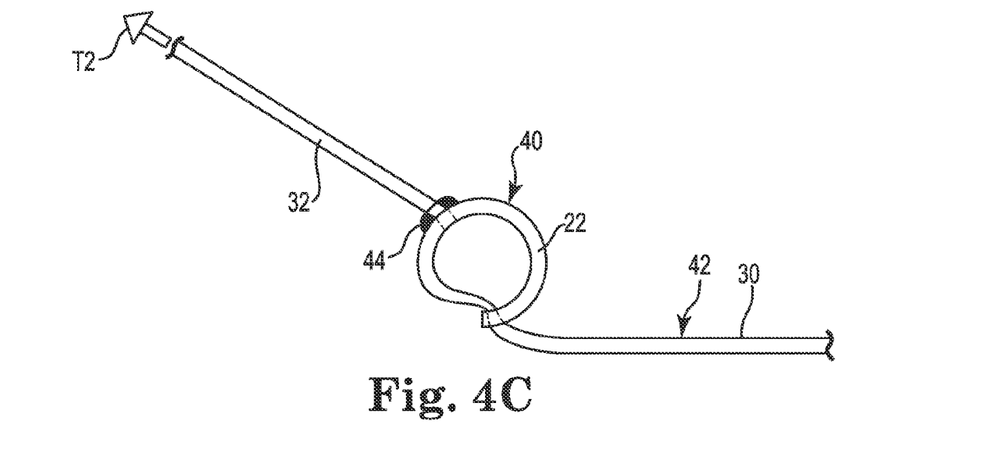
FIG. 4C is a top view of the incontinence treatment device illustrated in FIG. 4A with tension applied to a second extending member to loosen the cuff of the device.

FIG. 4C is a top view illustrating a second tension T2 applied to the second extending member 32 to draw the stopper 44 away from the slot 36, which expands the cuff 40 to relieve coaptation of the urethra to allow the user to urinate.

When implanted, the cuff 40 provides the user with the ability to pull on the first extending member 42 to achieve a continent state, and to subsequently pull on the second extending member 32 to transition the user into a state that allows urine to pass through the urethra.

In one embodiment, the cuff 40 is user-activated with each of the first and second extending members 42, 32, respectively, implanted to be accessible to the user such that user-applied tension T1 applied to the first extending member 42 will coapt the urethra to provide the user with a continent state, and user-applied tension T2 applied to the second extending member 32 will relieve the coaptation of the urethra and allow the user to urinate.

Figure 5:
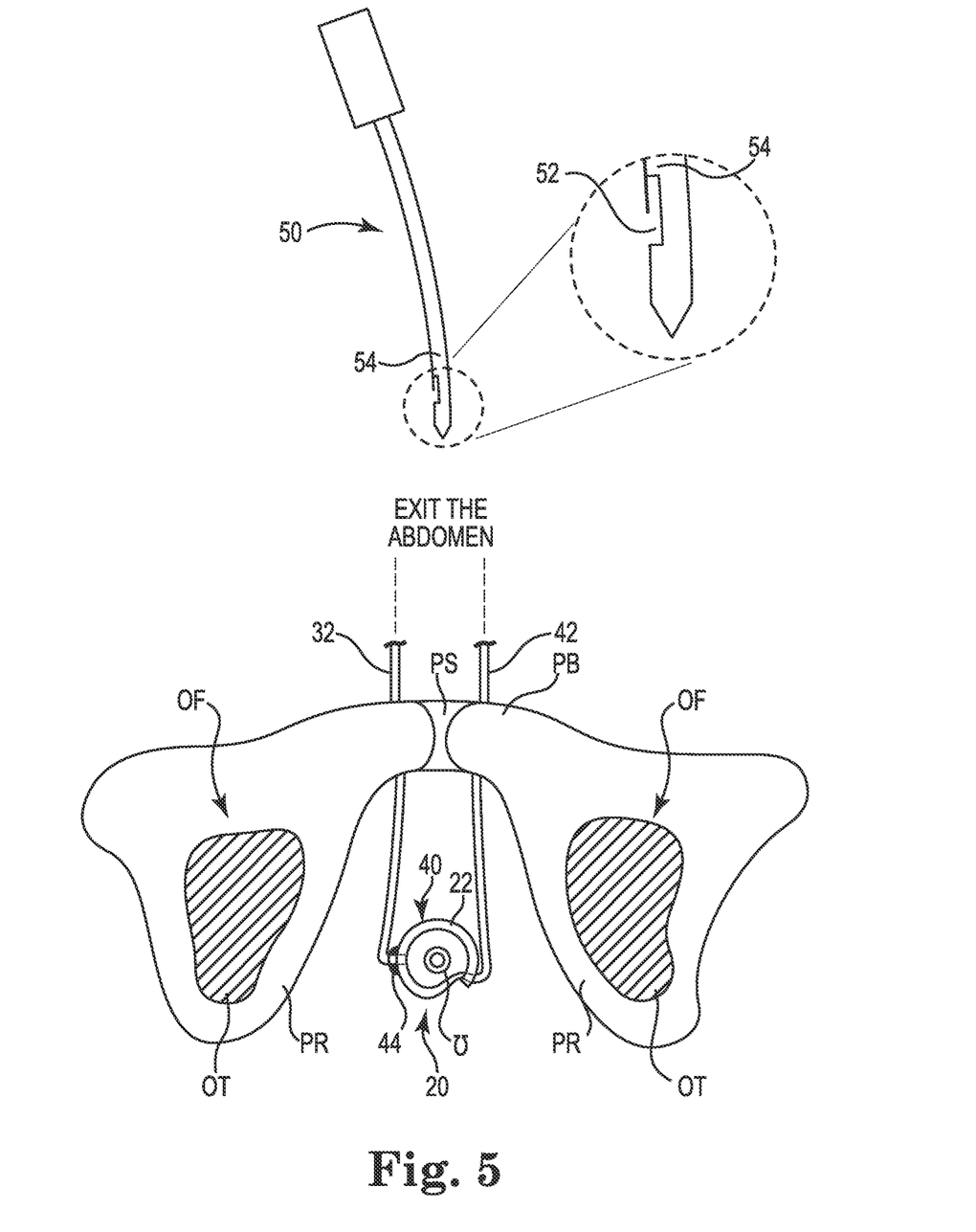
FIG. 5 is a schematic view of one embodiment of an incontinence treatment device with a cuff implanted around the urethra and extending members directed behind a pubic symphysis and through a wall of an abdomen.

FIG. 5 is a schematic view of one embodiment of the device 20 after implantation. The cuff 40 is implanted around the urethra U and the extending members 32, 42 are tunneled behind the pubic bone PB and project through a wall of the abdomen. The extending members 32, 42 are located in a user-accessible location outside the body. Tension applied by the user to the first extending member 42 tightens the cuff 40 to coapt the urethra and provide the user with a continent state. Tension applied by the user to the second extending member 32 loosens the cuff 40 to relieve the coaptation of the urethra and allow the user to urinate.

In one embodiment, the device 20 is implanted into the patient such that the cuff 40 surrounds the urethra U and the extending members 32, 42 exit through the skin of the abdomen of the user. In one the suitable implantation approach, a perineal incision (male) or a vaginal incision (female) is made, and tissue surrounding the urethra U is dissected to gain access to the urethra U. A portion of the device 20 is inserted into the incision. With reference to FIG. 1, the second end portion 30 is subsequently maneuvered around the urethra U and inserted through the slot 36 in the first end portion 28 to form the cuff 40 around the urethra U. A suitable tunneling device, such as a pointed introducer 50 or needle-like device, is inserted through the skin of the abdomen at an access point in an abdominal location that is superior to the pubic symphysis PS. The introducer 50 is tunneled downward toward the urethra U and exits the incision formed in the patient. One of the extending members 32, 42 is engaged with a T-slot 52 formed in an end portion 54 of the introducer 50, and the introducer 50 is retracted upwards behind the pubic bone PB and out of the access point formed in the abdominal location. This maneuver is repeated on the contralateral side, in which the pointed introducer 50 is inserted through the skin and into the abdomen at a second access point that is superior to the pubic symphysis PS and again tunneled downward to exit the incision formed in the patient. The other of the extending members 32, 42 is engaged with the slot 52 of the introducer 50, and the introducer 50 is retracted upwards behind the pubic bone PB and out of the second access point formed in the abdomen.

The perineal or the vaginal incision is closed. The extending members 32, 42 project outward from the abdomen through the access points formed in the abdominal locations. A suitable barrier is provided to prevent the transmission of bacteria into the abdominal locations. In other approaches, a prophylactic antibiotic is employed to reduce infection at the abdominal locations.

The first and second extending members 42, 32, respectively, are thus accessible to the user. Tension applied to the first extending member 42 will tighten the cuff 40 to coapt the urethra U. Tension applied to the second extending member 32 will expand the cuff 40 to allow the user to pass urine through the urethra U.

Figure 6:
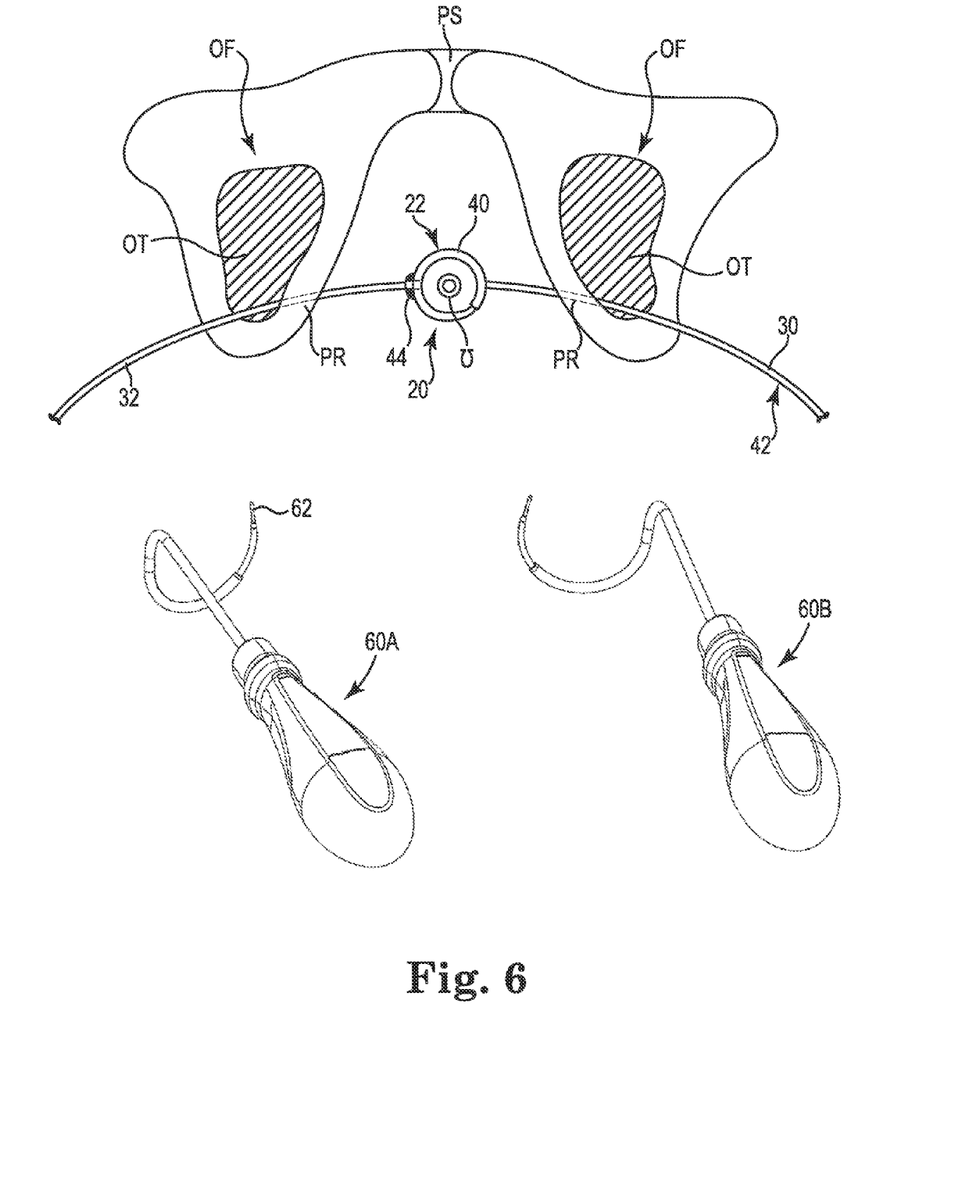
FIG. 6 is a schematic view of one embodiment of an incontinence treatment device with a cuff implanted around the urethra and extending members directed through obturator foramina and through a groin of a user.

FIG. 6 is a schematic view of one embodiment of the cuff 40 implanted around the urethra U with each of the extending members 32, 42 directed through one of the obturator foramina OF and out of the groin to a user-accessible location.

In one embodiment, the device 20 is implanted into the patient such that the cuff 40 surrounds the urethra U and the extending members 32, 42 extend through an obturator foramen and out of the skin of the groin. In one suitable implantation approach, a perineal incision (male) or a vaginal incision (female) is made, and tissue surrounding urethra is dissected to gain access to the urethra U. With reference to FIG. 1, the second end portion 30 is maneuvered around the urethra U and inserted through the slot 36 in the first end portion 28 to form the cuff 40 around the urethra U. The ends of the extending members 32, 42 are suitably tunneled through each of the obturator foramen OF and out of the skin in the region of the groin.

In one embodiment, an introducer 60A is employed in an "inside out" approach to tunnel the ends of the extending members 32, 42 out of the skin of the groin. For example, an end of the second extending member 32 is engaged with a tip 62 of the introducer 60A at a location outside of the incision (perineal for male or vaginal for female). The introducer 60A is suitable curved to allow the end of the extending member 32 to be directed behind the descending pubic ramus PR, through one of the obturator foramen OF, and out of the skin in the region of the groin. A similar maneuver is repeated on the contralateral side with a suitably formed second introducer 60B to direct the end of the extending member 42 through the other obturator foramen OF.

Another suitable approach directs an introducer through an "outside in" approach in which the introducer enters the skin in the groin region, penetrates the obturator foramen OF, and is directed around the descending pubic ramus PR until a tip of the introducer exits the incision. The tip of the introducer is coupled with an end of one of the extending members 32, 42, and the introducer is retrieved back through the incision, the obturator foramen OF, and the skin in the groin region. A similar maneuver is repeated on the contralateral side to place the other of the extending members 32, 42.

Thus, as illustrated in FIG. 6, each of the first and second extending members 42, 32, respectively, is implanted through one of the obturator foramen and extends to the skin to a user-accessible location.

Figure 7A:
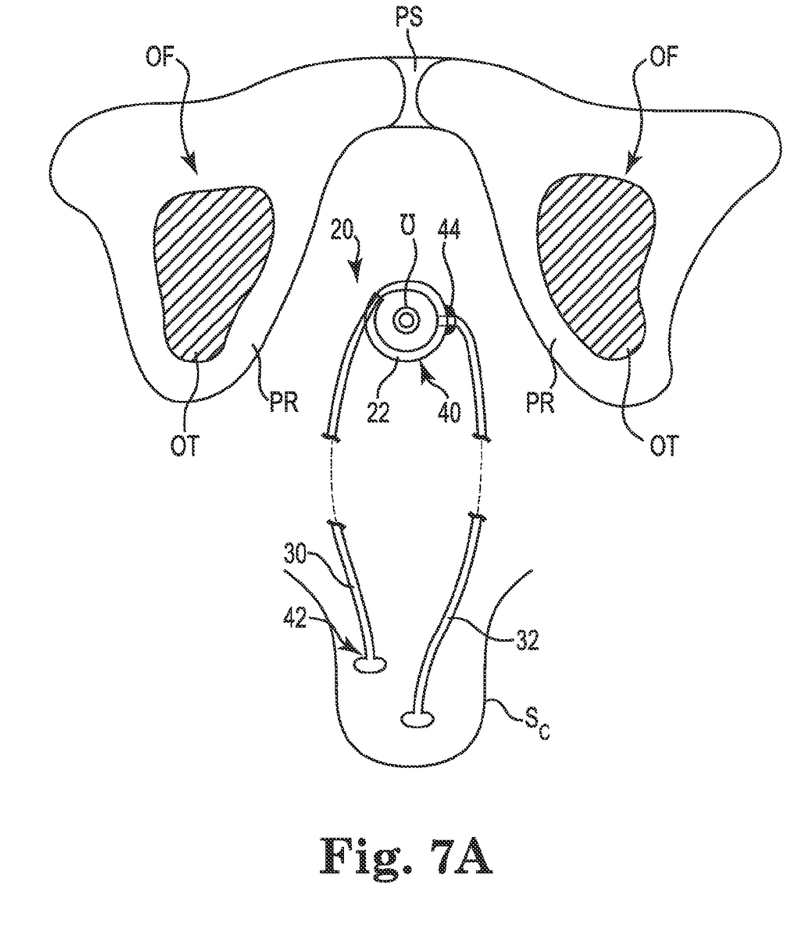
FIG. 7A is a schematic view of one embodiment of an incontinence treatment device with a cuff loosely implanted around the urethra and extending members implanted in a scrotum.
Figure 7B:
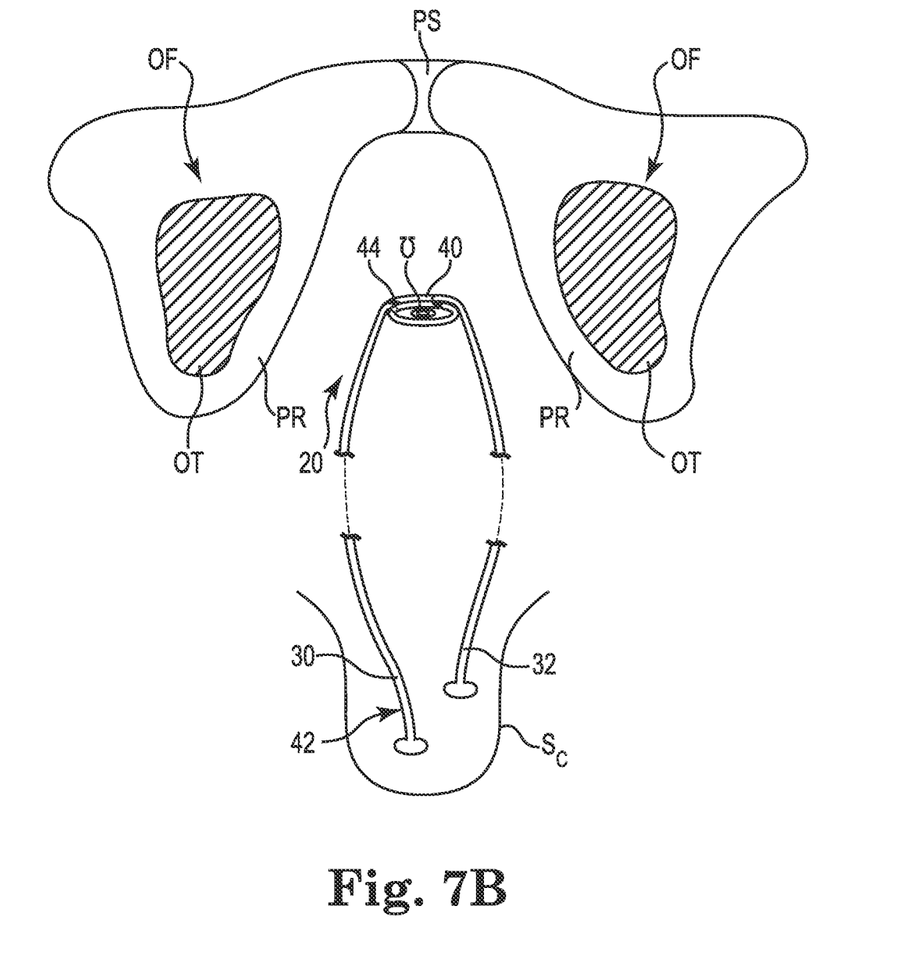
FIG. 7B is a schematic view of one embodiment of the incontinence treatment device illustrated in FIG. 7A with the cuff tightened around the urethra to provide the user with a continent state.

FIG. 7A is a schematic view of one embodiment of an open cuff 40 implanted around the urethra U and FIG. 7B is a schematic view of the cuff 40 coapting the urethra U.

In one embodiment, the extending members 32, 42 are implanted in a scrotum of a male user, and although implanted internal to the user, are accessible for selectively altering the user between a continent state and a urination state.

Similar to the approaches described above, an incision is made, and tissue surrounding urethra is dissected to gain access to the urethra U. The non-porous sheet 22 is maneuvered around the urethra U to form the cuff 40 around the urethra U. The ends of the extending members 32, 42 are directed into the scrotum Sc and the incision is closed.

The user pulls on the extending members 32, 42 through the skin of the scrotum to adjust the cuff 40 between the tightened and coapted state and the loosened and open states. FIG. 7A illustrates the second extending member 32 activated or pulled to open the cuff 40. In this configuration, the user is provided with an opened cuff 40 that allows the user to pass urine through the urethra U.

FIG. 7B illustrates the first extending member 42 tensioned or otherwise pulled to collapse the cuff 40 around the urethra U, which provides the user with a continent state.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of treating urinary incontinence, the method comprising:
    making an incision and exposing tissue of a urethra;
    inserting a non-porous sheet into the incision and forming a cuff around the urethra with the non-porous sheet by directing a first end of the non-porous sheet through a slot formed in a second end of the non-porous sheet;
    directing an extending member that is attached to the non-porous sheet to a location exterior of a pelvis;
    configuring the cuff to tighten around the urethra when pulling on the first end of the non-porous sheet;
    configuring the cuff to be loosely positioned around the urethra when pulling on the extending member; and
    implanting the cuff around the urethra, implanting the first end of the non-porous sheet through a first obturator foramen of a user, and implanting the extending member through a second obturator foramen of the user.

2. The method of claim 1, comprising placing the first end of the non-porous sheet and the extending member through skin of a user.

3. The method of claim 1, comprising placing the first end of the non-porous sheet and the extending member through an abdominal wall of the user.

4. A method of treating urinary incontinence, the method comprising:
    making an incision and exposing tissue of a urethra;
    inserting a non-porous sheet into the incision and forming a cuff around the urethra with the non-porous sheet by directing a first end of the non-porous sheet through a slot formed in a second end of the non-porous sheet;
    directing an extending member that is attached to the non-porous sheet to a location exterior of a pelvis;
    configuring the cuff to tighten around the urethra when pulling on the first end of the non-porous sheet;
    configuring the cuff to be loosely positioned around the urethra when pulling on the extending member; and
    implanting the cuff around the urethra and implanting the first end of the non-porous sheet and the extending member into a scrotum of the user.

* * * * *